United States Patent [19]

Harth, III et al.

[11] Patent Number: 4,682,397
[45] Date of Patent: Jul. 28, 1987

[54] HIGH TEMPERATURE PRESSURE VESSEL INSPECTION PROCEDURE

[75] Inventors: George H. Harth, III, Wadsworth; Gregory P. Zolton, II, Fairlawn; Robert L. Copen, Norton, all of Ohio

[73] Assignee: The Babcock & Wilcox Company, New Orleans, La.

[21] Appl. No.: 834,720

[22] Filed: Feb. 28, 1986

[51] Int. Cl.[4] .................... B23Q 17/00; B21C 43/00
[52] U.S. Cl. ........................... 29/407; 29/81 J; 29/81 F; 29/81 G
[58] Field of Search ............... 29/81 F, 81 G, 81 H, 29/81 J, 407; 51/71, 73 R, 326, 328

[56] References Cited

U.S. PATENT DOCUMENTS

| 1,122,731 | 12/1914 | Gilman et al. | 29/81 H |
| 2,058,229 | 10/1936 | Hogkins | 29/81 H |
| 3,331,114 | 7/1967 | Neufelder | 29/81 J |
| 4,200,947 | 5/1980 | Ali | 29/81 J |
| 4,445,248 | 5/1984 | Hait | 29/81 J |

Primary Examiner—Howard N. Goldberg
Assistant Examiner—Steven Nichols
Attorney, Agent, or Firm—R. J. Edwards; Michael L. Hoelter

[57] ABSTRACT

A method of inspecting a tube header bore comprises scoring an oxide scale layer within the bore using a hard scribing tool. The bore is then cleaned using one or more honing brushes having flexible bristles with carbide tips. After sufficiently cleaning the inner surface of the bore a florescent dye is applied to the surface for highlighting surface defects and a visual inspection is made. For easy access to the interior of the bore, the tube is cut at a point spaced from the bore. After the inspection is complete a new length of tube is connected such as by welding.

8 Claims, 4 Drawing Figures

HIGH TEMPERATURE PRESSURE VESSEL INSPECTION PROCEDURE

FIELD OF THE INVENTION

The present invention relates in general to boiler maintenance, and in particular to a new and useful method of inspecting a high temperature pressure vessel.

BACKGROUND OF THE INVENTION

High temperature pressure vessels such as boilers include tube headers which consists of heavy walled piping, generally about 20 inches in diameter and over three inches thick. An array of tubes may vary from approximately $\frac{3}{4}$ of an inch through $3\frac{1}{4}$ inch inside diameter and are typically 0.180 inches thick. Tubes are seated within bores in the header and are welded to the header. A change or step in diameter is created between the inside diameter of the tube and the inside diameter of the bore, the bore usually having a larger diameter than the inside of the tube.

It is known that after a period of use, a metal oxide film forms on the interior surfaces of the boiler tubes and tube header. This oxide scale exhibits hardness qualities beyond 60 Rockwell "C". Extreme care must be taken not to work harden this scale beyond its existing state. Scale removal must not radically distort the surface conditions of the base material either.

It is important however, to remove the oxide scale so as to permit inspection of the base material particularly within the tube header bores. This is because the surface of the bores within the tube headers are susceptible to cracking and these cracks are totally covered and obscured by the oxide scale.

One ordinary method for removing the scale is a mechanical one which requires cutting the tubes at an upper surface of the header and boring out the remaining tube stub. Boring equipment and cylinder hones would then be used to finish out the tube bore. A problem with this approach is that after the tube is replaced, the thick walled header must be stress relieved per ASME code. A field stress relief of this type would take days to perform and tens of thousands of dollars of cost, depending upon the size and thickness of the header.

Other methods of removing scale, in addition to physical removal of the tube, include the use of abrasive materials such as a sandpaper, the use of chemicals such as acids, and the use of stone hones. Each of these techniques however, have shortcomings. Friction from sandpaper heats up the oxide thereby making it even harder. Acid requires much time and eats away at the base material of the header and tubes. As noted above, physical removal of the tubes is extremely time consuming and expensive. Stone hones may break within the tubes or bores and this would cause even greater problems in trying to retrieve the breakage from the inside of boiler tubes.

SUMMARY OF THE INVENTION

The present invention is drawn to a method of inspecting the interior of tube header bores which include the steps of initially scoring or etching a line or lines into the oxide layer along the length of the area to be cleaned, using a carbide tipped brush for cleaning away the oxide layer with the brush being somewhat larger in diameter than the tube and the bore, supplying an appropriate dye to the cleaned area for highlighting any cracks or defects, and inspecting the area using fiber optics or other viewing equipment.

Once scored or etched, a plurality of brushes are used in succession each with finer grit values so that the scar lines from a preceeding brushing operation are smoothed away to reveal a surface suitable for dye treatment and inspection.

This invention is particularly advantageous in that a stepped area such as an enlargement in bore size can be cleaned and inspected by using the flexible brushes.

Accordingly, an object of the present invention is to provide a method of inspecting the interior of a tube header bore having a scale layer thereon which comprises rotating a honing brush having flexible bristles with hard abrasive tips in the header bore to remove the scale layer and to expose a clean surface for visible inspection. A further object of the invention is to provide a method wherein the scale is first scored and wherein after the clean surface is exposed, a dye for highlighting imperfections in the surface is applied. A still further object of the invention is to provide a method wherein the scale layer is cleaned by a succession of honing steps using brushes having increasingly finer grit. Another object of the invention is to provide a method wherein a tube extends partly into a tube header bore having an increase in diameter between the inside of the tube and the inside of the bore, the tube being cut off at a location spaced from the header bore and the honing brush being inserted through the narrower tube for access to the exposed part of the bore below the step. For this purpose, the brush is selected having a diameter which is about 10 to 20% larger than the diameter of the exposed bore.

The various features of novelty which characterized this invention are pointed out with particularity in the claims annexed to and forming a part of this disclosure. The advantage of this procedure being that the tube does not have to be cut out of the header and later replaced and stress relieved. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
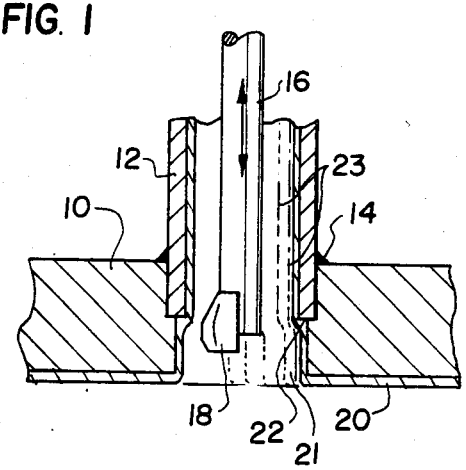
FIG. 1 is a side sectional view partially broken away showing a portion of the tube header having a bore therein with a tube connected in the bore, and further illustrating a first step of the present invention.

Referring to the drawings in particular, the invention embodied therein comprises a method of exposing and examining the inner surface of a tube header bore. As shown in FIG. 1, tube header 10 includes tube 12 partially inserted within bore 21 and seated against step 22 within this bore. Step 22 initiates a change in diameter from that of the smaller inside diameter of tube 12 to the larger inside diameter of bore 21 below step 22. Tube header 10 is constructed of thick walled material which is generally over 3 inches thick and tube 12 generally has an inside diameter ranging from about ¾ of an inch to 3¼ inches. After a number of years of use, a layer of scale 20 is formed within header 10 on the inside of tube 12 and on the exposed inside of bore 21. Scale 20 is a layer of hard metal oxide which generally has a hardness value of above 60 Rockwell "C".

An initial step of this invention is to score or etch line or lines 23 into the metal oxide layer 20 and at least in the exposed area of bore 21. This is done using rod 16 having a carbide scribing tool 18 connected at its end. Rod 16 is moved in the direction of the double arrow for producing each score line 23 and gradually rotated about its longitudinal axis should a plurality of score lines be desired. In order to access bore 21, tube 12 is cut off at a location spaced from header 10 and this way, when the boiler is reassembled, a new length of tubing is splice welded onto the stub portion of tube 12 still connected to header 10. This is desirable because no stress relieving is required for such an in-line splice.

Figure 2:
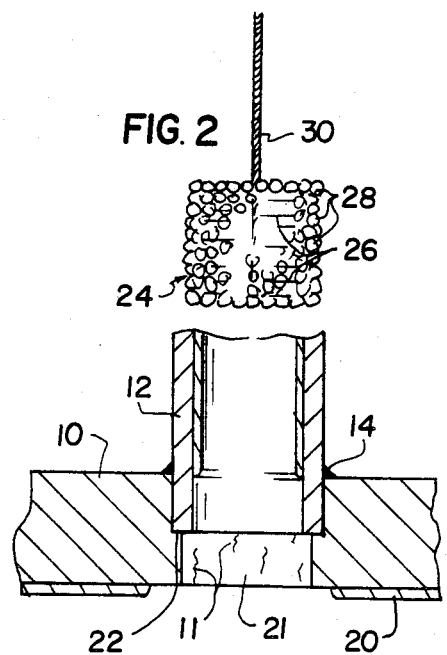
FIG. 2 is a view similar to FIG. 1 showing a further step of the invention utilizing a honing brush.

FIG. 2 illustrates the second step of the invention wherein a cleaning brush 24 is used to clean away scale layer 20 at least in the area of bore 21. FIG. 2 shows this area after the scale has been removed.

Brush 24 is of conventional design and includes a handle 30 which can be mounted to a drill or other device for rapidly rotating the brush first in one direction and then in an opposite direction. The brush includes a multiplicity of flexible bristles 26 each having an abrasive tip 28. Tips 28 may be made for example of either boron carbide or silicon carbide and in various grit sizes. The diameter of brush 24 is selected to be from about 10% to about 20% larger than the diameter of the exposed portion of bore 21. Due to the flexibility of bristles 26, brush 24 can easily be inserted into the small diameter of tube 12 and still clean the large diameter of bore 21. The step or change in diameter from the inside of tube 12 to the exposed portion of bore 21 is generally about ¼ inch.

Figure 3:
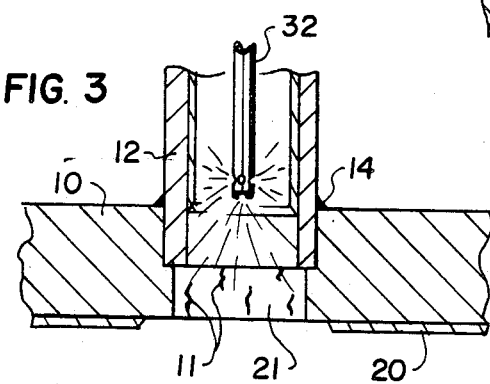
FIG. 3 is a view similar to FIG. 2 showing a still further step of the invention wherein a florescent dye is applied to the interior of the bore for highlighting cracks or other defects in the surface of the bore.

The cleaning away of oxide scale 20 reveals cracks 11 which may exist in the exposed area of bore 21. To better highlight these cracks, and as shown in FIG. 3, the cracks are bathed with a florescent dye of known properties which highlight cracks 11 or any other surface imperfections. The dye can be administered for example using a spray nozzle 32 having apertures for bathing the entire area inside tube 12 and inside bore 21 which has been cleansed of scale.

Figure 4:
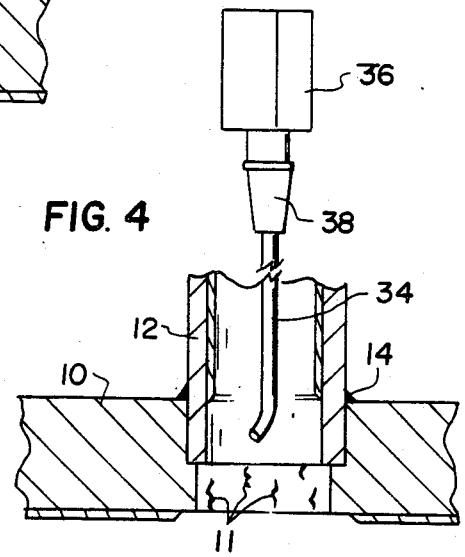
FIG. 4 is a view similar to FIG. 3 showing a final step of the inventive method wherein the bore is viewed using a fiber optic arrangement.

FIG. 4 shows the final step of the invention wherein a fiber optic scope having a fiber 24 is utilized to visually inspect the inner surface of the bore, and particularly to discover the existance of cracks 11. Fiber 34 for example, can be connected to a video or motion picture camera 36 over an adaptor 38.

In accordance with a refinement of the invention, a plurality of brushes 24 are generally used in sequence with decreasing grit coarseness. Preferably a brush 24 having for example 20 grit boron carbide tips 28 is initially used. With this brush in bore 21, handle 30 is rotated first in one direction and then in an opposite direction until most of the oxide scale and score lines 23 are removed. This is accomplished by undercutting oxide layer 20 via the softer material exposed by score lines 23. However due to the coarseness of 20 grit boron carbide, the brush itself leaves scribe marks in the softer underlying material which should be removed for accurate testing. To accomplish this a less course brush having 40 grit silicon carbide tips may be utilized. As with the first brush, is rotated in both directions until the scarring from the previous honing step has been removed.

For further polishing of the exposed portion of bore 21, a fine brush with, for example 60 grit silicon carbide tips is utilized to remove any further scarring which may have been produced by the previous brushing operations. The surface of the bore and interior tube 12 is now sufficiently clean for receiving the florescent dye shown in FIG. 3 and for the optical examination shown in FIG. 4.

While a specific embodiment of the invention has been shown and described in detail to illustrate the application of the principles of the invention, it will be understood that the invention may be embodied otherwise without departing from such principles.

What is claimed is:

1. A method for inspecting a tube header bore in a tube header, which has a scale layer deposited thereon, comprising:

rotating a first honing brush having flexible bristles with hard abrasive tips of a course grit in said header bore to remove said scale layer and to expose a clean surface inside said bore;

visually inspecting said clean surface of said bore;

applying a dye to said clean surface of said bore for highlighting any surface defects in said clean surface;

etching at least one line into said scale layer prior to rotating said first honing brush in said bore;

rotating a second honing brush having flexible bristles with hard abrasive tips of a relatively finer grit in said header bore after honing with said first brush, said tube header comprising a tube extending partly into said header bore and leaving an exposed portion of said header bore, the inner diameter of said tube being less than that of said exposed portion of said bore, said honing brushes being inserted through said tube for engaging said exposed portion of said bore; and, cutting off a portion of said tube at a location spaced from said header.

2. A method according to claim 1 including, after visually inspecting said clean surface of said bore, welding a new length of tubing onto said tube which partly extends into said header bore.

3. A method according to claim 2 wherein said scribe line is scored into said scale layer in an axial direction with respect to said bore and said tube, and further comprising removing said scale layer and said scribe line using said first mentioned honing brush, said first mentioned honing brush producing scar lines in parts of said exposed portion of said bore and using said second honing brush to remove said scar lines.

4. A method of inspecting a tube header bore in a tube header, having a scale layer deposit thereon, said tube header having a tube extending partly into said bore and leaving an exposed area of said bore, said tube having an inner diameter smaller than the inner diameter of said exposed area of said bore, said method comprising:

rotating a honing brush having flexible bristles with hard abrasive tips in said header bore to remove said scale layer and to expose a clean surface inside said bore, positioning said honing brush so as to remove said scale layer from said exposed area of said bore through said tube; and, forming at least one score line in said scale layer prior to rotating said honing brush in said bore, said score line being formed in an axial direction with respect to said tube and said bore.

5. A method according to claim 4 further comprising applying a florescent dye to said clean surface of said bore before visually inspecting said clean surface.

6. A method according to claim 5 further comprising cutting a portion of said tube at a location spaced from said header for enabling access to said clean surface by said honing brush and for said visual inspection.

7. A method according to claim 6 further comprising using a plurality of honing brushes with hard abrasive tips of successively finer grit for engaging said exposed area of said bore.

8. A method according to claim 7 wherein a first of said honing brushes to be used has carbide tips of 20 grit size, a second of said brushes to be used has carbide tips of 40 grit size and a third of said brushes to be used has carbide tips of 60 grit size.

* * * * *